United States Patent [19]

Rommel et al.

[11] Patent Number: 5,703,248

[45] Date of Patent: Dec. 30, 1997

[54] PROCESS FOR THE SELECTIVE TRIHALOGENATION OF KETONES USEFUL AS INTERMEDIATES IN THE SYNTHESIS OF THIOPHENES

[76] Inventors: Jeffrey S. Rommel, 1503 Lakeside, Wheaton, Ill. 60187; James T. Traxler, 917 Forest Ave., Evanston, Ill. 60202; Richard R. Boettcher, 21 W. 105 22nd St., Lombard, Ill. 60148

[21] Appl. No.: 451,285

[22] Filed: May 26, 1995

Related U.S. Application Data

[63] Continuation of Ser. No. 349,760, Dec. 5, 1994, abandoned, which is a continuation of Ser. No. 215,873, Mar. 21, 1994, abandoned, which is a continuation of Ser. No. 102,672, Aug. 5, 1993, abandoned, which is a continuation of Ser. No. 972,055, Nov. 5, 1992, abandoned, which is a continuation of Ser. No. 883,052, May 8, 1992, abandoned, which is a continuation of Ser. No. 527,606, May 22, 1990, abandoned.

[51] Int. Cl.⁶ .................... C07C 45/00; C07D 333/00

[52] U.S. Cl. .................... 549/62; 570/253; 570/261; 568/393; 568/388; 568/419

[58] Field of Search .................... 570/253, 261; 549/62; 568/393, 388, 419

[56] References Cited

FOREIGN PATENT DOCUMENTS 1129943  5/1962  Germany.
1139823  11/1962  Germany.

OTHER PUBLICATIONS

DeBuyck et al. Bull. Chim. Soc. Belg. V. 96, No. 9, 663 ff, (1987).

*Primary Examiner*—Gary Geist
*Attorney, Agent, or Firm*—Gabriel Lopez; Lynn Marcus-Wyner; Allen E. Norris

[57] ABSTRACT

The present invention concerns a novel process for the selective trihalogenation of ketones employing organic halogen salts.

12 Claims, No Drawings

PROCESS FOR THE SELECTIVE TRIHALOGENATION OF KETONES USEFUL AS INTERMEDIATES IN THE SYNTHESIS OF THIOPHENES

This application is a continuation of application Ser. No. 08/349,760 filed Dec. 5, 1994 now abandoned, which is a continuation of application Ser. No. 08/215,873 filed Mar. 21, 1994 now abandoned, which is a continuation of application Ser. No. 08/102,672 filed Aug. 5, 1993 now abandoned, which is a continuation of application Ser. No. 07/972,055 filed Nov. 5, 1992 now abandoned, which is a continuation of application Ser. No. 07/883,052 filed May 8, 1992 now abandoned, which is a continuation of application Ser. No. 07/527,606 filed May 22, 1990 now abandoned.

The present invention concerns a novel process for the selective trihalogenation of ketches and olefins or precursors thereof and novel compounds prepared thereby which are useful in the preparation of intermediates for agrochemicals.

In particular, the invention relates to a process for selectively mono-halogenating a hydrogen bearing carbon atom located α to a carbonyl group and selectively dihalogenating across an olefinic bond located α to a carbonyl group which comprises halogenation in the presence of an organic halogen salt which produces halide ions soluble in an organic solvent.

In a further aspect, the invention relates to the selective trihalogenation of compounds comprising the structural element A:

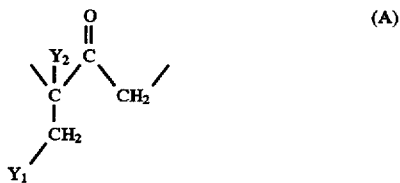

wherein $Y_1$ and $Y_2$ together form a bond or $Y_1$ represents halogen and $Y_2$ represents H or precursors thereof to produce compounds comprising structural element B:

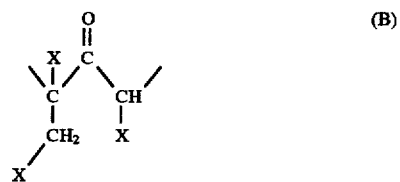

wherein each X is halogen, which comprises halogenation in the presence of organic halogen salt which produces halide ions soluble in an organic substrate.

Previous methods for direct trihalogenation of compounds comprising the structural unit (A) involving "neat" halogenation, two-phase systems, radical inhibitors or the like, yielded significant amounts (up to 40%) of impurities. Similar drawbacks were encountered when employing a two step process culminating in halogenation of the corresponding mono-halogenated compound (cf DE Pat. 1,139,823; DE Pat. 1,129,943; Bull. Soc. Chim. Belg., 96, 663 (1987)).

The process of the present invention significantly reduces the presence of impurities in many cases to 5% or less.

Especially preferred halogen salts in the performance of the process according to the invention are organic ammonium halide salts e.g. mono-to tetra substituted ammonium halides especially chlorides where trichlorination is desired. Such preferred salts can be represented by the formula XX:

wherein X is halogen and each of $R_1, R_2, R_3, R_4$ is hydrogen or an organic group whereby at least one is other than hydrogen, especially an optionally substituted alkyl group phenyl or benzyl. Depending on the substitution pattern, the compounds of formula X will be in the form of a quaternary ammonium salts or in the form of an amine acid addition salts. X is preferably chlorine and the preferred organic group is optionally substituted alkyl phenyl or benzyl. Examples of such compounds of formula X are tetrabutylammonium chloride, tributylmethylammonium chloride, triethylamine hydrochloride, 2-methoxyisopropylamine hydrochloride, t-butylamine hydrochloride, tripropylamine hydrochloride, trimethylphenylammonium chloride, tributylphenylammonium chloride, dimethylditallowammonium chloride, dicocodimethylammonium chloride, dipropylamine hydrochloride.

Precursors of structural elements (A) are those which convert under the reaction conditions of the trihalogenation to (A). Examples of such precursor compounds are those containing The structural element C:

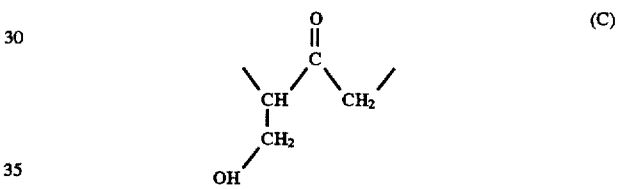

which on dehydration converts to structural element (A).

In will be readily appreciated by those skilled in the art that the process according to the present invention can be employed with all organic compounds which comprise the requisite structural element and are otherwise susceptible to halogenation on said element.

The conditions employed in carrying out the process according to the invention will depend on the nature of the organic compound to be halogenated and organic halogen salt to be employed.

Halogenation is conveniently performed with halogen gas. The reaction may be performed in a solvent inert under the reaction conditions such as halogenated aliphatic compounds such as carbon tetrachloride, dichloromethane, or ethers such as diethylether, t-butylethylether.

Alternatively, the organic halogen salt can be dissolved in the compound to be halogenated if this is a liquid.

The organic halogen salt is conveniently employed in amounts of e.g. 2 to 20 mole % exceptionally 50 mole % with respect to the compound to be halogenated.

In general, smaller amounts of salt are required when a structural element A is being halogenated, with larger amounts for trihalogenation of precursors.

The reaction is performed at ambient or moderately elevated temperatures e.g. 20° to 100° C.

A particularly preferred embodiment of the present invention comprises a process for the preparation of a compound of formula I:

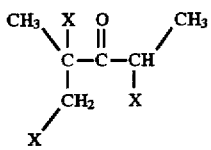

wherein X represents halogen, which comprises halogenating a compound of formula II:

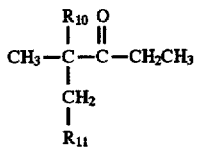

wherein, $R_{10}$ represents hydrogen and $R_{11}$ represents hydroxy or $R_{10}$ and $R_{11}$ represent an extra bond, in the presence of a compound of formula III:

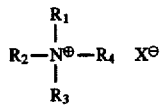

wherein X represents halogen, $R_1$, $R_2$, $R_3$ and $R_4$ represent independently hydrogen or optionally substituted alkyl, phenyl or benzyl whereby at least one of $R_1$, $R_2$, $R_3$, $R_4$ is other than hydrogen. X is preferably chlorine.

The compounds of formula I are new and also form part of the invention. The reaction is carried out in an inert solvent e.g. as above.

Alternatively, the catalyst may be dissolved in the compound of formula II.

The reaction may be performed at moderately elevated temperatures e.g. 20° to 100° C.

Preferred catalysts of formula III are tetrabutyl ammonium chloride and tripropylamine hydrochloride.

The compounds of formula II are known and may be prepared for example by reaction of diethylketone with formaldehyde ($R_{10}$=H,$R_{11}$=OH) or reaction of propene with prop ionic acid or propionyl chloride ($R_{10}$+$R_{11}$=bond). Alternatively, the compounds of formula II may be prepared by selective oxidation of the primary-secondary glycols ($R_{10}$=H, $R_{11}$=OH) or catalyzed vapor phase reaction of diethyketone or methyl propionate with formaldehyde.

As mentioned above, the compound of formula II wherein $R^{10}$ and $R^{11}$ represent an extra bond may be prepared by dehydration of the corresponding compound wherein $R_{10}$=H and $R_{11}$=OH. Processes for preparing compounds of formula II are described in Bull. Soc. Chim. France, 838 (1947); Tetra. Letters, 24, 5009 (1983); Sekiyu Gakkaishi, 29 (1), 72 (1986).

The organic ammonium chloride salts of formula III are known and may be prepared in conventional manner for the preparation of quaternary ammonium salts.

The compound of formula I as illustrated above is particularly useful in the preparation of 2,4-dimethyl-2,3-dihydro-thiophen-3-one of the formula IVa:

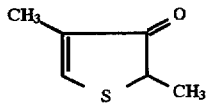

[This compound may also exist in its tautomeric enol-form]

The invention therefore also concerns a process for preparing a compound of formula IVa or IVb

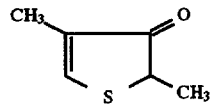

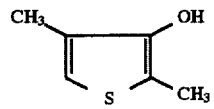

which comprises cyclization of a compound of formula I

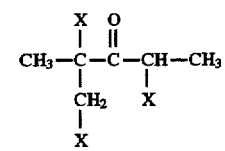

wherein each X is independently halogen in the presence of sulfide ions.

This process also forms part of the invention.

As stated, this reaction is effected by reacting the compound of formula I with sulfide ions.

Suitable sources of sulfide ions are sulphides of alkali or alkaline earth metal sulfides such as sodium sulfide ($Na_2S$) or sodium hydrogen-sulfide (NaHS) or combinations thereof. Alternatively, hydrogen sulfide with a base may be employed.

This reaction may advantageously be carried out in the presence of an inorganic or organic base e.g. an alkali metal hydroxide such as NaOH, or a primary, secondary or tertiary amine such as methoxypropylamine, triethylamine and the like. Alternatively, the sulphide itself may act as sole base. The reaction may be carried out at temperatures of –40° to 100° C. A suitable reaction temperature is for example from 20° to 90° C., e.g. from 60° to 90° C.

The compound of formula I, $H_2S$ and the base may be and preferably are employed in equivalent amounts.

Alternatively, the compound of formula I may be reacted with e.g. 1 eq Nails+2 eq NaOH; 1 eq NaHS+2 eq($C_2H_5$)$_3$N;1.5 eq $Na_2S$; 3 eq NaHS; 3 eq NaOH+1 eq $H_2S$.

The process is conveniently effected in a solvent which is inert under the reaction conditions, e.g. in water, an alkanol such as methanol, a chlorinated hydrocarbon such as 1,2-dichloroethane or mixtures thereof.

Preferably in the preparation of IVa and IVb each X in the compound of formula I is the same halogen; however compounds wherein the X's represent different halogens, e.g. 4-bromo-1,2-dichloro-methylpentan-3-one, may also be employed. These may be prepared using methods disclosed or referenced above.

The reaction to prepare the compounds Ira and IVb can also be carried out as a continuous process for example as typified by Example 3e. Depending on reaction conditions, a certain amount of the tetrahydro form of compounds IV may be obtained which can readily be converted to the IVa <–> IVb form according to the procedures of EP Appl. No. 88109474.2; Pub. No. EP 296463, the contents of which are hereby incorporated by reference.

The compound of formula IVa (2,4-dimethyl-2,3-dihydrothiophen-3-one) or IVb is a useful intermediate in preparation of herbicidally active compounds, in particular N-(2,4-dimethylthienyl-3-yl)-N-(1-methoxyprop-2-yl)-chloracetamide (hereinafter designated thienylchloracetamide).

In preparation of thienylchloracetamide, the compound of formula IVa, IVb or a mixture thereof is reacted with 1-methoxy-2-propylamine to produce N-(1-methoxyprop-2-yl)-2,4-dimethylamino-thiophene.

Alternative methods for its production and its reaction to corresponding methoxypropylated compound are described in EP Appl. No. 88109474.2; Pub. No. EP 296463, the contents of which are hereby incorporated by reference.

Reaction of N-(1-methoxyprop-2-yl)-2,4-dimethylaminothiophene with chloracrytchloride to yield thienylchloracetamide is described in EP Appl. No. 85810348.4; Pub. No. EP 210320 the contents of which are hereby incorporated by reference.

The invention may be illustrated by the following examples in which temperatures are in degrees Centigrade.

EXAMPLE 1

(a) preparation of 1-hydroxy-2-methylpentan-3-one 4.31 g (50mmol) of 3-pentatone and 0.0023 g (3.5 meq) of triethylamine are mixed and heated to 45° C. to 50° C. Pareformaldehyde 0.30 g (10 mmol) is added incrementally. After all the pareformaldehyde is added, the reaction mixture is stirred for an additional 2h. Glacial acetic acid (0.035 g) is added to reach a pH of 6.0 to 7.0.

The reaction mixture is stripped of excess 3-pentatone under vacuo (30 mm Hg). The residue is vacuum distilled to yield the title composed.

(b) Preparation of 2-methyl-1-pentene-3-one

1-Hydroxy-2-methyl-3-pentanone (730.22 g, mol), $H_3PO_4$(35.94 g, mol), hydroquinone (9.12 g, mol), and Copper powder (9.12 g, mol) are mixed and heated to reflux, 88° C. The product, 2-methyl-1-pentene-3-one and water are collected overhead. The layers are separated, and the organic layer is dried overnight with $CaSO_4$ (60 g). The organic layer is filtered to remove the $CaSO_4$ to yield the title compound.

EXAMPLE 2

Preparation of 1,2,4-trichloro-2-methylpentanone-3 (compound of formula I)

9.39 g (95.7 mmol) of 2-methyl-1-pentan-3-one and 2.52 g (9.07 mmol) of tetrabutylamonium chloride are mixed and flushed with argon. Chlorine gas is introduced under the surface of the liquid reaction mixture at a rate of 0.25 g/min. Upon addition of the chlorine the reaction mixture exotherms to a temperature of 60° C. The temperature of the reaction mixture is maintained at 60° to 70° C. and the addition of chlorine continued for a further 2 hrs. The resulting product is purged with argon to remove residual gases. Gas chromatographical analysis against a purified sample of the title compound revealed selectivity to be 96.9%.

The reaction mixture is washed with 3×10 ml water to remove the catalyst and the organic phase dried over $Mg(SO_4)_2$ to yield the title compound.

$^1$H nmr (90 MHz, $CDCl_3$, r TMS) δ5.11 (1 H, q, J=6.6 Hz), 5.09 (1 H, q, J=6.6 Hz), 3.96 (1 H, d, J=0.0 Hz), 3.95 (1 H, d, J=0.0 Hz), 3.90 (2 H, s), 1.92 (3 H, s), 1.83 (3 H, s), 1.69 (3 H, d, J=6.8 Hz), 1.67 (3 H, d, J=6.8 Hz).

EXAMPLE 3

Preparation of 2,4-dimethyl-3-hydroxythiophene and 2,4-dimethyl-2,3-dihydro-thiophen-3-one.

a) Using $H_2S$/NaOH

A solution of 21.9 g 1,2,4-trichloro-2-methyl-pentanone-3 (0.1 mole) in 85 ml of MeOH, 35 ml of water, and 0.6 ml of HOAc is saturated under argon with $H_2S$ (0.78 mole absorbed) at room temperature. To this solution is added 30 ml (0.1 mole) of NaOH solution (20 g in 85 ml of MeOH and 40 ml of $H_2O$) during 7 minutes while maintaining an $H_2S$ flow of 210 ml/min (absorbed 0.41 mole) and pH<6.5 (mostly 5.7–6.0). The temperature of reaction mixture rises from 25° C. to 40° C. during the addition. After a 15-minute stirring period, an additional 45 ml (0.15 mole) of NaOH solution is slowly added (10 minutes) under the same conditions, while a further 0.69 mole of $H_2S$ is absorbed. At this point the original trichloroketone content has decreased to 2.3%. After stirring as is for 0.5 hr., an additional 0.05 mole of NaOH solution is added at ca. 32° C. and pH<6.5, and the reaction mixture absorbed a further 0.34 mole of $H_2S$. After stirring as is for ca. 15 minutes, excess $H_2S$ is removed by entrainment with argon for 20–30 minutes. An additional 0.2 mole of NaOH solution is then added and the reaction mixture is stirred at 65°–70° C. for 3 hours. Rotary evaporation of MeOH, followed by base extraction, acidification, and re-extraction into methyl t-butyl ether gives the product solution, an aliquot of which is analyzed by internal standard GLC to obtain the desired products IV in 92.4% yield and 97.4% purity.

b) Using Sodium Sulfide and Sodium Hydroxide

A solution of 30 g of 1,2,4-trichloro-2-methylpentan one-3 (0.141 mole of 95.7%) in 120 ml of MeOH is treated dropwise under argon with a solution of 37.3 g (0.155 mole) of $Na_2S.9H_2O$ in 50 ml of water over 30 minutes at 20° C. The light yellow reaction mixture is stirred as is for 1.25 hours (pH=8.6) and then a solution of 4N aqueous NaOH is added over 1.5 hours to a constant pH of 10.5. Methyl t-butyl ether (75 ml) is added to the reaction mixture followed by sufficient 18% HCl solution to give pH 6.2, and the layers are mixed and separated. The aqueous layer is extracted under argon 2 times more with 75 ml of methyl t-butyl ether, and the combined organic layers are washed with saturated NaCl solution. After drying by passage through a short column of $MgSO_4$, the resulting solution is analyzed by internal standard GLC. The desired product is present in 89.0% yield and 89.8% purity.

nmr ($CDCl_3$, δ, ppm): Enol (IVb): 6.55 (s, 1 H); 8.45 (bs, 1 H); 2.30 (s, 3 H); 2.17 (d, 3 H, J=0.98 Hz). Ketone (IVa): 7.95 (s, 1 H); 3.68 (q, 1 H, J=7.32 Hz); 1.55 (d, 3 H, J=7.32 Hz).

c) Using Sodium Hydrosulfide and Triethylamine

Triethylamine (15.3 ml, 0.1 mole) is added to a solution of 14.3 g (0.19 mole of 100%) $NaSH.H_2O$ in ca. 60 ml of MeOH, and the slightly cloudy solution is added under argon to a solution of 2.04 g (0.1 mole) of 1,2,4-trichloro-2-methylpentanone-3 in 60 ml of MeOH, beginning at room temperature. The exotherm is allowed to rise to 38° C. over the addition period (1 hour) and controlled with a cool water bath. After the addition, the reaction mixture is stirred at room temperature until no more 1,2,4-trichloro-2-methylpentanone-3 is visible by GLC (ca. 1 hour). The suspension is filtered and the NaCl is washed several times on the filter with MeOH. The combined MeOH solutions are concentrated on the rotary evaporator to give a red oil which is redissolved in 100 ml of methylene chloride, washed with water and concentrated with a rotary evaporator. The resulting 24.26 g of oil is analyzed by GLC (area percent) to contain the desired product in 80.9% yield.

d) Using Sodium Sulfide and NaOH (alternative to b) above)

An aqueous solution of Na$_2$S (3.69M, 0.255 mole) in 50 ml of MeOH is added dropwise over ca. 1 hour to a solution of 1,2,4-trichloro-2-methylpentanone-3 (0.23 mole) in 140 ml of MeOH at ≦30° C. at a rate such as to maintain pH ca. 6.5. The solution is stirred for an addition hour at ≦30° C. and 130 ml of 4N NaOH is added at ≦30° C. and the MeOH is removed from the solution with a rotary evaporator at ≦45° C. bath temperature. Neutral by-products were removed from the aqueous solution by extraction with heptane, and the aqueous layer is acidified with 2M HCl to pH 6.5. Extraction of the product with t-butylmethyl ether followed by drying over Na$_2$SO$_4$ gives a solution containing the desired compounds IV in 82% yield, determined by internal standard GLC analysis.

e) Continuous Preparation

A CSTR at 60°–100° C. (preferably 90° C.) is fed with 1,2,4-trichloro-2-methylpentanone-3, 10% aqueous sodium hydrosulfide, and 25% aqueous sodium hydroxide at mole ratious of 1:1.45:1.6, respectively, maintaining the pH at 6–7 over a residence time of 3–4 hours. The effluent from this reactor is fed into a second CSTR at 60°–100° C. (preferably 90° C.), where it is treated with a second 25% aqueous sodium hydroxide solution at the rate of 0.25 equivalent, based upon the starting 1,2,4-trichloro-2-methytpentanone-3, maintaining the pH at ca. 8.0. The residence time in this reactor also is maintained at 3–4 hours to give a two-phase product solution containing no 1,2,4-trichloro-2-methylpentanone-3, and a 96% yield of cyclized material consisting of 90% of Compounds IV and 10% of 2,4-dimethyl-3-ketotetrahydrothiophene. The latter also is convertible in high yield by the process of EP 296463 to Compounds IV.

What is claimed is:

1. A process for the selective trihalogenation of a compound of formula II:

$$\begin{array}{c} R_{10}\ O \\ |\ \ \ || \\ CH_3-C-C-CH_2CH_3 \\ | \\ CH_2 \\ | \\ R_{11} \end{array} \quad (II)$$

wherein $R_{10}$ represents hydrogen and $R_{11}$ represents hydroxy or $R_{10}$ and $R_{11}$ represent an extra bond, to yield a compound of formula I $$\begin{array}{c} CH_3 \ \ X\ \ O\ \ \ \ CH_3 \\ \ \ \ \backslash\ |\ \ ||\ \ / \\ \ \ \ \ C-C-CH \\ \ \ /\ \ \ \ \ \ |\ \ \ \ \ \ | \\ \ CH_2\ \ \ \ \ \ X \\ / \\ X \end{array} \quad (I)$$

wherein X represents halogen, which comprises halogenating at a temperature range of about 20° to 100° C., the compound of formula II with molecular halogen in the presence of an organic halogen salt of the formula III $$\begin{array}{c} R_1 \\ | \\ R_2-N^{\oplus}-R_4 \ \ X^{\ominus} \\ | \\ R_3 \end{array} \quad (III)$$

wherein X is halogen and each of $R_1$, $R_2$, $R_3$, and $R_4$ is independently hydrogen or optionally substituted alkyl, phenyl, or benzyl wherein at least one of $R_1$, $R_2$, $R_3$, and $R_4$ is other than hydrogen, in the range of 2 to 20 moles % which produces halide ions soluble in an organic solvent.

2. A process of claim 1 wherein each X is chlorine and at least one of $R_1$, $R_2$, $R_3$, and $R_4$ is alkyl.

3. A process for the preparation of a compound of formula I:

$$\begin{array}{c} CH_3 \ \ X\ \ O\ \ \ \ CH_3 \\ \ \ \ \backslash\ |\ \ ||\ \ / \\ \ \ \ \ C-C-CH \\ \ \ /\ \ \ \ \ \ |\ \ \ \ \ \ | \\ \ CH_2\ \ \ \ \ \ X \\ / \\ X \end{array} \quad (I)$$

wherein X represents halogen which comprises halogenating at about 20° to 100° C. a compound of formula II:

$$\begin{array}{c} R_{10}\ O \\ |\ \ \ || \\ CH_3-C-C-CH_2CH_3 \\ | \\ CH_2 \\ | \\ R_{11} \end{array} \quad (II)$$

wherein $R_{10}$ represents hydrogen and $R_{11}$ represents hydroxy or $R_{10}$ and $R_{11}$ represent an extra bond, with molecular halogen in the presence of a compound of formula III:

$$\begin{array}{c} R_1 \\ | \\ R_2-N^{\oplus}-R_4 \ \ X^{\ominus} \\ | \\ R_3 \end{array} \quad (III)$$

wherein X is halogen and each of $R_1$, $R_2$, $R_3$, and $R_4$ is independently hydrogen or optionally substituted alkyl, phenyl, or benzyl wherein at least one of $R_1$, $R_2$, $R_3$, and $R_4$ is other than hydrogen which produces halide ions soluble in an organic solvent.

4. A process of claim 3 wherein at least one of $R_1$, $R_2$, $R_3$, and $R_4$ is alkyl.

5. A process of claim 3 wherein each X is chlorine.

6. A process of claim 3 wherein the compound of formula III is tetrabutylammonium chloride or tripropylamine hydrochloride.

7. A process for preparing a compound of formula IVa or IVb (IVa) — 2,4-dimethyl-3-oxo thiophene structure with CH$_3$, O, S, CH$_3$ (IVb) — corresponding enol form with OH, S, CH$_3$, CH$_3$ which comprises cyclising in the presence of sulfide ions a compound of formula I $$\begin{array}{c} CH_3 \ \ X\ \ O\ \ \ \ CH_3 \\ \ \ \ \backslash\ |\ \ ||\ \ / \\ \ \ \ \ C-C-CH \\ \ \ /\ \ \ \ \ \ |\ \ \ \ \ \ | \\ \ CH_2\ \ \ \ \ \ X \\ / \\ X \end{array} \quad (I)$$

wherein each X is halogen.

8. A process of claim 7 wherein each X is the same.

9. A process of claim 7 wherein each X is chlorine.

10. A process for preparing N-(2,4-dimethylthien-3-yl)-N-(1-methoxyprop-2-yl)-chloracetamide comprising the steps of a) cyclising in the presence of sulfide ions a compound of formula I

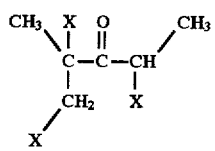 (I)

wherein each X is halogen to produce a compound of formula IVa or IVb;

b) reacting a compound of formula IVa or IVb with 1-methoxy-2-propylamine to produce N-(1-methoxyprop-2-yl)-2,4-dimethylamino thiophene; and c) N-chloracetylating N-(1-methoxyprop-2-yl)-2,4-dimethylamino thiophene with chloracetylchloride.

11. A process of claim 10 wherein the compound of formula I is prepared by halogenating a compound of formula II

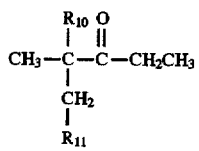 (II)

wherein $R_{10}$ represents hydrogen and $R_{11}$ represents hydroxy or $R_{10}$ and $R_{11}$ represent an extra bond, with molecular halogen in the presence of a compound of formula III

 (III)

wherein X is halogen and each of $R_1$, $R_2$, $R_3$ and $R_4$ is independently hydrogen, or optionally substituted alkyl, phenyl, or benzyl wherein at least one of $R_1$, $R_2$, $R_3$, and $R_4$ is other than hydrogen.

12. A process of claim 11 wherein at least one of $R_1$, $R_2$, $R_3$, and $R_4$ is alkyl and each X is chlorine.

* * * * *